United States Patent
Geldrich (10) Patent No.: US 10,264,949 B2
(45) Date of Patent: Apr. 23, 2019

(54) FINGER ENGAGEMENT ASSEMBLY FOR SECURING AND MANIPULATING A HANDHELD DENTAL TOOL IN A USER'S HAND

(71) Applicant: Kristel K. Geldrich, Loveland, CO (US)

(72) Inventor: Kristel K. Geldrich, Loveland, CO (US)

(*) Notice: Subject to any disclaimer, the term of this patent is extended or adjusted under 35 U.S.C. 154(b) by 0 days.

(21) Appl. No.: 15/582,898

(22) Filed: May 1, 2017

(65) Prior Publication Data

US 2018/0310805 A1 Nov. 1, 2018

(51) Int. Cl.
*A61B 1/00* (2006.01)
*A61B 1/247* (2006.01)

(52) U.S. Cl.
CPC .......... *A61B 1/00066* (2013.01); *A61B 1/247* (2013.01); *A61B 2560/0425* (2013.01)

(58) Field of Classification Search
CPC ................ A61B 1/00066; A61B 1/247; A61B 2560/0425
USPC .......................................................... 433/141
See application file for complete search history.

(56) References Cited

U.S. PATENT DOCUMENTS

| | | | |
|---|---|---|---|
| 974,887 A * | 11/1910 | Huddle ................ | B43K 23/012 401/8 |
| 1,094,888 A * | 4/1914 | Ehrle ................... | B43K 23/012 15/443 |
| 3,402,984 A * | 9/1968 | Zazzara ............... | B43K 23/012 15/443 |
| 3,812,894 A * | 5/1974 | Bradbury ............... | B25B 15/02 81/436 |
| 5,944,433 A * | 8/1999 | O'Mara ............... | B43K 23/008 401/7 |
| 6,249,977 B1 * | 6/2001 | Knoop .................... | B26B 13/24 30/232 |
| 10,150,330 B1 * | 12/2018 | Pernici ................. | B43K 23/001 |
| 2011/0022038 A1 * | 1/2011 | Seshadri ............ | A61B 17/3207 606/7 |
| 2014/0112696 A1 * | 4/2014 | Osborne ............... | B43K 29/00 401/195 |

* cited by examiner

*Primary Examiner* — Matthew M Nelson
(74) *Attorney, Agent, or Firm* — Marsh Fischmann & Breyfogle LLP; Kent A. Lembke (57) ABSTRACT

A finger engagement assembly for supporting a handheld dental tool on a user's hand. The finger engagement assembly includes a mounting member with a cylindrical shaped body extending along a grip axis and having an aperture extending there through. The mounting member has an inner surface that interfaces with a dental tool and an outer surface that interfaces with a finger engagement. The finger engagement includes a rotational coupling extending about the mounting member and is operable to rotate relative to the mounting member about the grip axis. A post extends from the rotational coupling in a first direction and supports a crossbar. The crossbar extends across the backs of a user's index and middle finger and is functional to retain a handheld dental tool, such as a dental mirror, to a user's hand, while allowing the dental tool to rotate relative to the finger engagement.

20 Claims, 9 Drawing Sheets

FINGER ENGAGEMENT ASSEMBLY FOR SECURING AND MANIPULATING A HANDHELD DENTAL TOOL IN A USER'S HAND

BACKGROUND

1. Field of the Description

The present description relates, in general, to handheld dental instruments such as a dental mirror and, more particularly, to a gripping system or finger engagement assembly for use securing a dental mirror to a user's fingers so as to reduce physical strain on the user and also to improve ease of use or operation of the handheld dental mirror.

2. Relevant Background

While performing dental procedures, various dental professionals (e.g., dentists and dental hygienists) utilize a variety of small handheld tools for performing various functions such as cleaning, drilling and dispensing. The most commonly used dental tool may well be a handheld dental mirror. Dental mirrors are used to view areas in the mouth that are difficult if not almost impossible to view without the aid of such an instrument. Additionally, dentists and dental hygienists usually hold the dental mirror in addition to other tools such as a scraper or drill in their hands and are frequently manipulating the mirror to obtain a desired view.

The common dental mirror includes an elongated handle with a circular cross section attached to an angled mirror. Many dental mirrors have a serrated portion or similar feature located on a gripping section for helping the user to grip and manipulate the tool. Although various grips are possible, dental mirrors are usually gripped in a user's hand in a similar fashion to a pencil. That is, a user, such as a dental hygienist will grip a dental mirror between the thumb, forefinger and middle finger. However, unlike a pencil, a dental hygienists will frequently be rotating or otherwise changing their grip on a dental mirror. For example, while examining and cleaning a patient's teeth, a dental hygienist may rotate or change the orientation of the dental mirror within her or his hands a multitude of times. The numerous and repeated manipulation of a dental mirror can lead to fatigue and other ailments in a user's hand. Although, seemingly small, this frequent and repeated stress could lead to more serious conditions such as carpal tunnel syndrome.

In addition to easing the stress due to repeated use of a dental mirror, it is also desirable to be able to keep a dental mirror in a user's hand while they use that same hand to grab other tools, perform other operations, and the like. That is, a dentist's or dental hygienist's efficiency can be greatly increased by not having to put down their dental mirror every time they need to use that hand for another procedure. Additionally, having a way to maintain a dental mirror on a relatively fixed relation to a user's hand without needing to maintain a firm grip on the mirror could further increase efficiency, productivity and a patient's experience by allowing the user to maintain the mirror in their hand while freeing up the use of their hand for other uses.

SUMMARY

Briefly, the inventor designed a finger engagement assembly or dental instrument grip system for mounting on handheld dental tools, objects or other devices, such as dental mirrors, drills, dispensers, or other devices. The finger engagement assembly addresses the previously discussed problems with use of handheld dental instruments including physical strain, ease of use, and/or freeing the user's hand, fingers, and/or thumb for other tasks while not requiring the user to set down the dental instrument (e.g., the finger engagement assembly can retain a dental instrument, such as a dental mirror, in the users hands without the user needing to grasp the dental mirror).

The finger engagement assembly is adapted for effective securing of a dental instrument to a user's hand, while facilitating specific movement (e.g., rotation) of that instrument relative to the hand for performing various dental or other procedures. In some embodiments, the finger engagement assembly includes a mounting member that is cylindrical shaped with an aperture extending there through along its longitudinal axis. The mounting member couples to a dental instrument such as a dental mirror providing an attachment for a finger bracket. The finger bracket can include multiple components that interface with a human hand. For example, the finger bracket can include a rotational coupling that mounts over or interface with the mounting member and is operative to rotate relative to the mounting member. In this regard the rotational coupling is rigidly fixed to the mounting member and, thus, the dental mirror and can rotate around the dental mirror. A post extends from the rotational coupling and supports a crossbar at distance from the rotational coupling and, thus, the dental mirror. When a user holds a dental mirror with a finger engagement assembly, the crossbar extends across the backs of a user's fingers and retains or secures the dental mirror to the user's hand. The finger bracket remains substantially in a fixed relationship to the user's fingers and together with the mounting member allows the user to rotate the dental mirror to different orientations relative to her/his hand.

More particularly, a finger engagement assembly or apparatus is provided for supporting a dental mirror in a user's hand. The apparatus includes a mounting member including a tubular body for receiving a handle of the dental mirror, and the tubular body (or at least an inner core portion) is formed of an elastomer such as a rubber such that its inner diameter (ID) can be elastically deformed/enlarged to receive the handle of the dental mirror during use of the apparatus. The apparatus also includes a finger bracket for mating with fingers of the user's hand. Further, the apparatus includes a rotational coupling (or rotational coupling assembly may be used interchangeably herein) attached to an outer surface of the mounting member. The finger bracket extends outward from the rotational coupling, and the rotational coupling is adapted to allow the finger bracket to rotate at least 180 degrees (e.g., often 360 degrees in either direction) about a central axis of the tubular body of the mounting member.

In some implementations of the apparatus, the rotational coupling includes an inner element affixed to the mounting member and also includes an outer element rotatably coupled to the inner element. Typically, the finger bracket is rigidly coupled to the outer element of the rotational coupling. Further, in some cases, the outer element of the rotational coupling is rotatable in either direction for 360 degrees relative to the inner element of the rotational coupling.

In many cases, the finger bracket is designed to include a post extending from a first end attached to the rotational coupling to a second end spaced apart a distance from the rotational coupling. Further, the finger bracket includes an elongated cross bar attached to the second end of the post to be transverse (e.g., orthogonal or some other useful angle) to a longitudinal axis of the post. In some implementations of the apparatus, the post has a length of at least 0.5 inches and extends outward at an angle in the range of 45 to 90 degrees as measured between the longitudinal axis of the post and a central axis of the tubular body. The post and/or cross bar may be formed to be rigid in some cases while other useful implementations of the apparatus may be designed such that at least one of the post and the cross bar is flexible and formed of a plastic or elastomeric material. In these or other cases, the cross bar may have a length of at least 0.75 inches, may be attached at a center point to the second end of the post, and may be arcuate or linear in shape.

In various embodiment, the finger engagement assembly includes a retaining system for suspending and manipulating a dental instrument relative to a user's hand. The retaining system includes a dental instrument having an outer surface that extends along a longitudinal axis and a rotational coupling member, coupled to the outer surface such that the rotational coupling member can rotate, about the longitudinal axis, relative to the dental instrument. The retaining system further includes, a post extending from the rotational coupling member. The post having a first end opposite the rotational coupling member. The retaining system also includes a crossbar coupled to the first end of the post. When the retaining system is mounted on the dental instrument and held by the user, the crossbar contacts a first finger at a first contact point and contacts a second finger at a second contact point.

In some implementations of the retaining system, the crossbar extends in a straight line between a first end and a second end and is normal to the longitudinal axis. In various implementations, the post can extend from the rotational coupling member at an acute angle. In some, implementations the crossbar curves toward the longitudinal axis.

DETAILED DESCRIPTION OF THE PREFERRED EMBODIMENTS

Briefly, the present description is directed to a finger engagement assembly for securing a handheld dental tool (such as dental mirror, drill, pick and/or the like) in a user's hand. The finger engagement assembly was developed in part because the inventor was exploring ways to reduce stress associated with holding and manipulating dental tools for extended periods of time. Particularly, the inventor was searching for ways that a user could comfortably hold a dental tool, such as a mirror, for a long period of time. Additionally, the inventor was searching for a way to secure a dental tool to a user's hand while still allowing the user to use that same hand for other tasks without having to put the dental tool down. That is, each time the user needed to pick up some other object or instrument, she/he wouldn't have to put the dental tool down and then subsequently pick it back up after finishing another task.

Figure 1A:
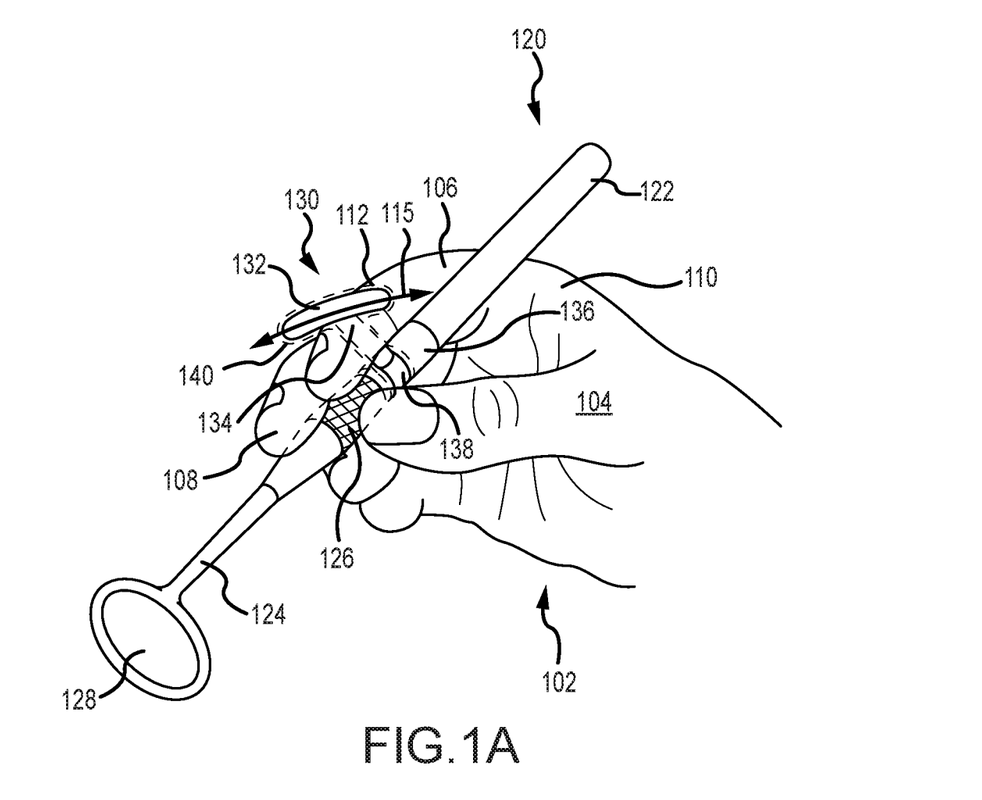
FIG. 1A illustrates, with a front view of a user's hand, a finger engagement assembly mounted on a dental mirror during its use or when being worn by a user.

FIG. 1A illustrates one embodiment of a finger engagement assembly 130 mounted on a dental mirror 120 while being held in the hand 102 of a user. The user is a human such that the hand 102 is a human hand, with the right hand being shown in this example, but the finger engagement assembly 130 and dental mirror 120 can also be held in the left hand of the user. The present description mainly describes the finger engagement assembly 130 in relation to a handheld dental mirror 120 for illustrative purposes. However, it will be understood that the finger engagement assembly 130 could be similarly configured to fit over a variety of handheld instruments including other dental instruments such as picks, drills and/or the like. Therefore, the present disclosure is not limited to dental mirrors or dental tools, and the concepts described herein are intended to be illustrative and not limiting.

FIG. 1A shows the user's hand holding a dental mirror 120 with the finger engagement assembly 130 from a front perspective view. The finger engagement assembly 130 as shown in FIG. 1A includes a mounting member 136 having a tubular body (shown in FIG. 3A). The mounting member 136 slides over dental mirror 120 and is positioned in a desired location on the handle 122 of the dental mirror 120 by the user. Typically, dental mirrors 120 include a handle 122 coupled to a neck portion 124 that secures the mirror 128 in an angled orientation to the handle 122. That is, the mirror 128 is angled back toward the handle 122. The handle 122 can further include a serrated section 126, located near the neck 124 that aids a user in securely gripping the dental mirror 120. A user can position the mounting member 136 over the handle 122 such that a portion of the serrated section 126 is left exposed and the grip or finger engagement assembly 130 is located closer to the neck 124 than the end of the handle 122.

It is desirable for the mounting member 136 to fit securely over the handle 122 of the dental mirror (or other dental tool). Hence, as will be discussed in more detail below, the mounting member 136 can be formed from an elastic material. Further, in this regard, the inner diameter of the mounting member's tubular body is slightly smaller than the outer diameter of the handle 122, and the tubular body is formed from an elastic material (or at least its inner portion is formed of an elastic material such as when an elastic insert is provided within a more rigid (e.g., plastic) outer housing).

When the finger engagement assembly 130 is slid onto the dental tool 120, manually or by a user, the mounting member 136 is adapted to elastically expand to receive the tool 120 and to securely couple with the handle 122 (e.g., as it attempts to elastically return to its at rest inner diameter (ID)).

In an alternative embodiment, the mounting member 136 can have a hinge and/or a snap-fit configuration. In this embodiment, the finger engagement assembly 130 has a first configuration where the mounting member 136 is in an open state, such that its tubular body is split in half. The finger engagement assembly 130 is then attached to the dental instrument (e.g., dental mirror 120) by snapping the two halves of the mounting member's tubular body around the handle 122 of the dental mirror 120. In other embodiments, the mounting member 136 can take on other shapes such as polygonal cross-sectional configurations (e.g., triangular shaped tube) and is sized to securely couple with the dental mirror 120 based on its outer diameter, and based on the particular material used for the engagement or mounting member 136.

The finger engagement assembly 130, as shown in FIG. 1A, also includes a crossbar 132 connected to the mounting member 136 by post 134 (e.g., the crossbar 132 may be an elongated member with a circular, rectangular, or other shaped cross section and together with the post 134 generally form a tee), and the crossbar's inner surfaces will engage a user's fingers 106, 108 as shown during use. The post 134 is attached to the mounting member 136 by a rotational coupling 138. In this regard, the crossbar 132, post 134, and rotational coupling 138 are rigidly connected to each other forming a unitary finger bracket 140. The finger bracket 140 is mounted on mounting member 136 to rotate relative to mounting member 136 and, thus, can also rotate relative to the handle 122. In the illustrated embodiment, the post 134 extends from the rotational coupling 138 in a direction that is normal to mounting member 136 and handle 122. When the finger engagement assembly 130 is held by the user as shown, the user's index finger 106 (e.g., forefinger) and middle finger 108 are positioned on opposite sides of the post 134. The posterior (which may also be known as the palmar area) side of the index finger 106, middle finger 108, and thumb 104 contact the mounting member 136 and handle 122. The anterior (which may also be known as the dorsal area) side of the index finger 106 and the middle finger 108 are contacted by the crossbar 132 (i.e., by its inner surfaces). In this regard, the index and middle fingers 106, 108 are positioned/captured between the crossbar 132 and the mounting member 136 and are, in practice, rotatably coupled to or positionable relative to the handle 122.

When a user's fingers 106, 108 are positioned between the crossbar 132 and handle 122, the finger bracket 140 can rotate about the mounting member 136, while remaining relatively stationary to fingers 106, 108. In such a configuration, a user holding the dental mirror 120, with the finger engagement assembly 130 mounted thereon, can use their fingers 106, 108 and thumb 104 to change the orientation of the mirror 128 without needing to rotate or otherwise move their hand 102. Specifically, the finger bracket 140 is coupled to the dental mirror 120 through the rotational coupling 138 in a fixed relative position but such that the dental mirror can be angularly rotated in either direction around path 115 relative to the finger bracket 140 and user's hand/fingers. The finger bracket 140 can rotate 360° and/or rotate continuously around the mounting member 136 in either direction. In other embodiments, the rotation of the finger bracket 140 to the mounting member 136 can be limited. For example, the finger bracket 140 can be limited to rotate only 180° about the mounting member 136. In an implementation such as this, a mechanical stop, such as a partial groove located on the rotational coupling 138 and a pin/ledge on the mounting member 136, can be used to limit rotation. Although, other means of limiting rotation are also possible.

Figure 1B:
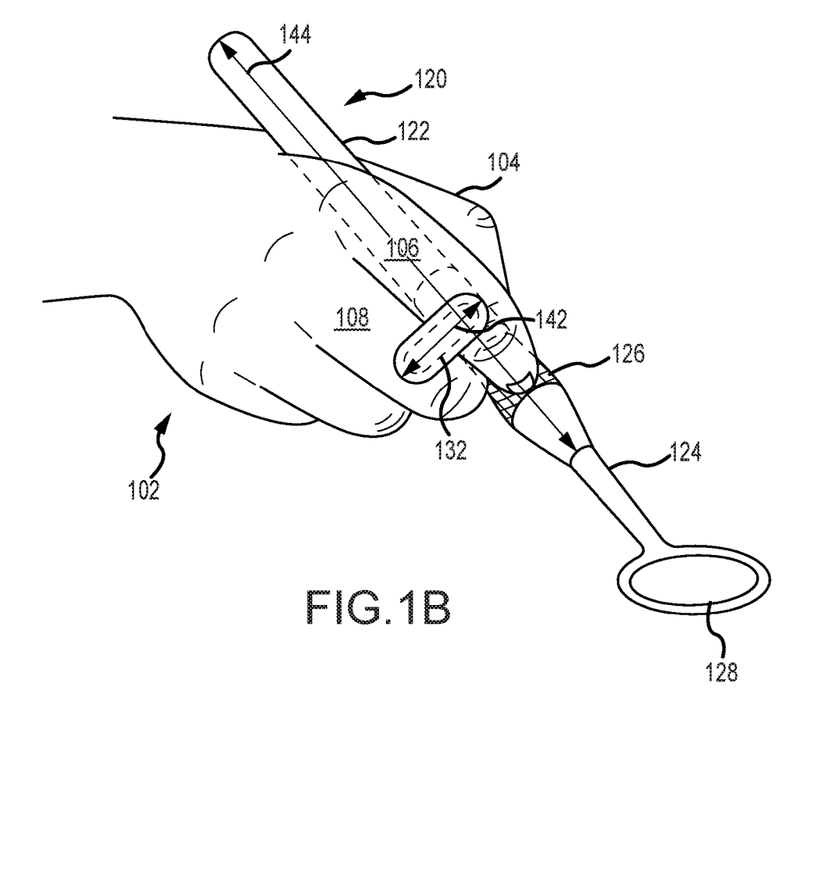
FIG. 1B illustrates, with a side view of a user's hand, a finger engagement assembly mounted on a dental mirror during its use or when being worn by a user.

FIG. 1B illustrates the finger engagement assembly 130 on the dental mirror 120 from a side perspective view. Specifically, in this view, the crossbar 132 and anterior portion of the hand 102 are shown. The crossbar 132 engages the anterior (dorsal) area of the index 106 and middle 108 fingers. In the illustrated embodiment, the crossbar 132 extends lengthwise in a direction that crosses the backs of the index 106 and middle 108 fingers (e.g., traverse to the fingers 106, 108). That is, the length 142 of the cross-bar 132 extends longer in the direction across the fingers 106, 108 (hereafter referred to as fingers 106, 108 unless specifically referenced) than the direction along the length of the fingers 106, 108. The crossbar 132 extends at least partially across the anterior side of the fingers 106, 108 but, in the illustrated embodiment, does not extend across the entire width of the fingers 106, 108. However, in an alternative embodiment, the crossbar 132 can extend across the entire width of the anterior side of the fingers 106, 108. To this end, the crossbar 132 can have a length in the range of 0.25 to 1.5 inches. Further, in other embodiments, the crossbar 132 can be curved inward (i.e., toward the mounting member 136) to wrap around at least a portion of the fingers 106, 108 (shown in FIG. 5A) to provide further support. In various embodiments the crossbar 132 is formed from a compliant/elastic material such that it conforms to the anterior side of the fingers 106, 108.

As illustrated in FIG. 1B, the crossbar 132 is positioned such that when worn by a user the crossbar 132 engages the fingers 106, 108 between the distal phalanx (tip of the finger) and middle phalanx (middle joint). That is, the crossbar 132 sits behind the fingernail and in front of the middle joint (i.e., middle phalanx) on the fingers 106, 108. The crossbar 132 is positioned such that its length 142 is substantially normal to the handle axis 144. In other embodiments, the crossbar 132 can be positioned such that its length 142 can be positioned at various angles relative to the handle axis 144. For example, the crossbar 132 may be rotated to form a 45 degree angle between the length 142 and handle axis 144. In other embodiments, the crossbar can take on other shapes, such as being circular, semi-circular, and/or the like, rather than the planar shape shown.

Figure 1C:
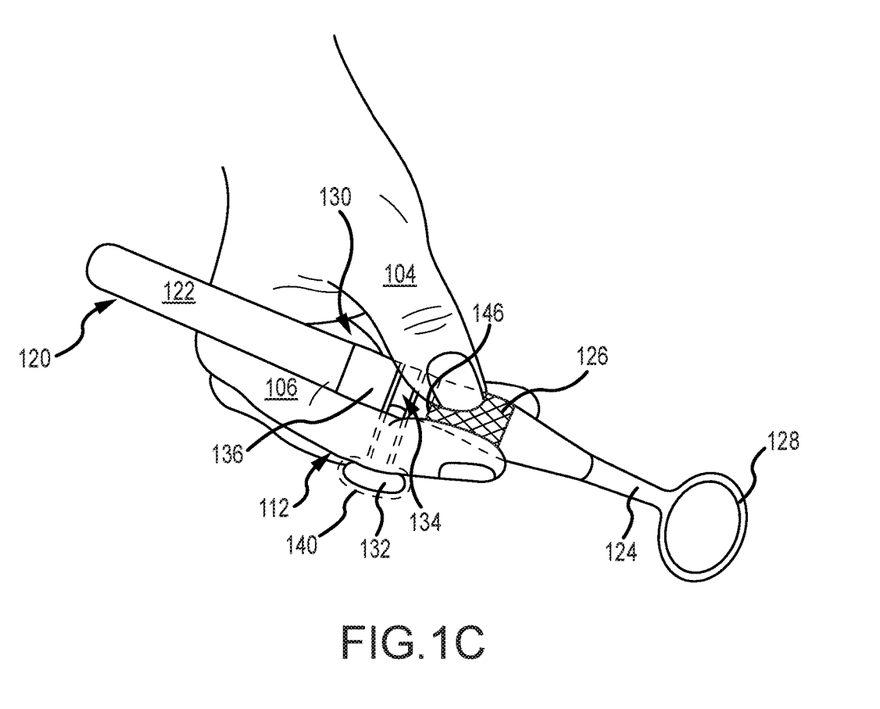
FIG. 1C illustrates, with a top view of a user's hand, a finger engagement assembly mounted on a dental mirror during its use or when being worn by a user.

FIG. 1C illustrates the finger engagement assembly 130 mounted on the dental mirror 120 being held by a user from a top-side perspective view. The mounting member 136 is positioned over the handle 122 such that at least a portion of the serrated section 126 is exposed between the front 146 of the mounting member 136 and the neck 124. In this embodiment, the finger bracket 140 is located closer to the front 146 of the mounting member such that when the grip 130 is mounted on the dental mirror 120 and held by a user the user's fingers 106, 108 contact at least a portion of the serrations 126. In this regard, the user can rotate the finger bracket 140 relative to the mounting member 136 and handle 122 by twisting (e.g., applying force) the serrations 126. In other embodiments, the mounting member 136 can extend to cover the entirety of the serrations 126, and the user can rotate the dental mirror 120 relative to the finger bracket 140 by twisting or applying force to the mounting member 136.

Figure 2:
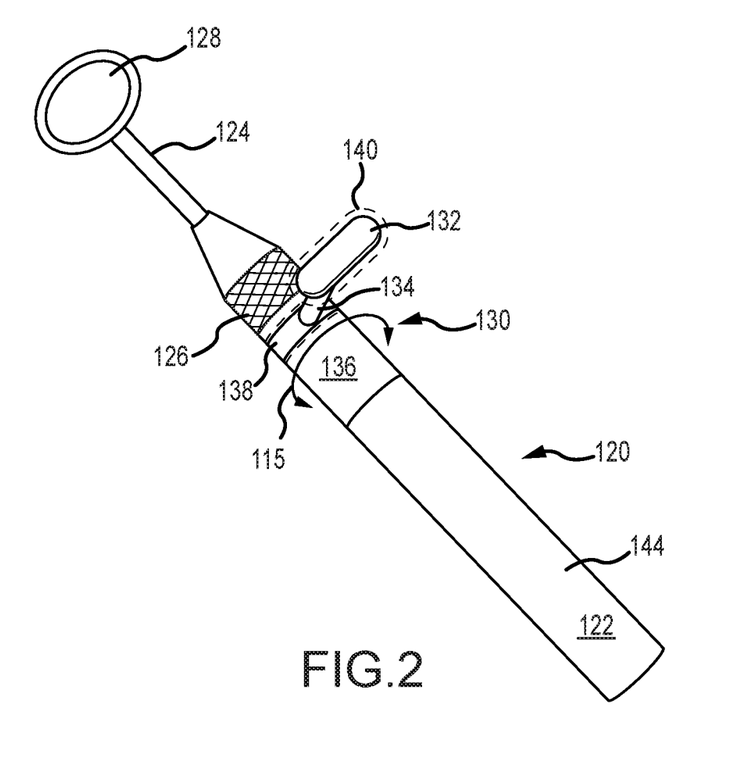
FIG. 2 illustrates, with a perspective view, a finger engagement assembly mounted on a dental mirror.

FIG. 2 illustrates the finger engagement assembly 130 mounted on a dental mirror 120 from a top-side perspective view. Particularly, the post or arm 134 can be seen extending between the rotational coupling 138 and the crossbar 132. In this embodiment, the post 134 is cylindrical and extends substantially normal to the handle axis 144. The post 134, crossbar 132 and rotational coupling 138 (together the finger bracket 140) can be a single component. The finger bracket 140 or individual components thereof (e.g., post 134, crossbar 132) can be flexible or elastic. In this regard, the finger bracket 140 can adapt or conform to a user's fingers 106, 108. Specifically, the post 134 can bend, stretch, extend, twist and otherwise deform to so as to accommodate to a user's specific grip or unique hand structure, while stiff securely retaining the user's fingers 106, 108 to the dental mirror 120. For example, when a user grabs the dental mirror 120 having a finger engagement assembly 130 mounted thereon, the finger bracket may deform such that it is positioned on a user's fingers as shown in FIGS. 1A-1B. This may entail flexing, bending, twisting, or other deformation of a few degrees and/or extension or compression of a few percent.

In alternative embodiments, the finger bracket 140 may deform to greater extents. In yet other embodiments, the finger bracket 140 or individual components thereof (e.g., post 134, crossbar 132) may be rigid and experience substantially no deformation. The finger bracket 140 can be formed from a wide variety of materials including various polymers such as elastic rubbers, silicone rubbers, plastics, and/or the like. The mounting member 136 can be formed from a similar material to the finger support 140.

In alternative embodiments, the mounting member 136 can be formed from a different material than the finger support 140. For example, the mounting member 136 can be formed from a plastic such as nylon, poly-propylene or other relatively low friction and elastic material. In this regard, the mounting member 136 is configurable be able to expand slightly to fit over the dental mirror handle 122, while securely gripping or coupling to the exterior surface of the handle 122 such that the mounting member 136 is rigidly coupled to the handle 122 so as to not move under normal application of force by a user to rotate the finger bracket 140. In this embodiment, the finger bracket 140 can also be formed from a similar plastic material such as poly-propylene. Specifically, the mounting member 136 and the finger bracket 140 are separate parts. This way, when the rotational coupling 138 is assembled over the mounting member 136, the finger bracket 140 is able to rotate relative to the non-moving mounting member 136 and, thus, is able to also rotate relative to the handle 122. The specific rotational mechanisms will be discussed in more detail in relation to FIG. 6 below.

In an alternative embodiment, the finger bracket 140 can be assembled from individual parts comprising the crossbar 132, post 134 and the rotational coupling 138. In this regard, the rotational coupling 138 can be formed from lower friction and more rigid material relative to the post 134 and/or crossbar 132. For example, the rotational coupling 138 may be formed from a plastic such as nylon or polypropylene and the post 134 and/or rotational coupling 132 may be formed from an elastic rubber. The various components can be chosen from materials that can be sterilized by standard methods such as autoclave (i.e., steam), ethylene oxide, gamma ray, and/or the like. In this embodiment, the more rigid rotational coupling 138 can help rigidly couple the finger bracket 140 to the mounting member 136, while still allowing the rotational coupling 138 to rotate relative to the mounting member 136. An elastic post 134 and crossbar 132 can increase conformance of these components to a user's hand and allow these components to deform relative to the rotational coupling 138, while securely retaining the user's fingers to the dental mirror 120.

In various embodiments the rotation coupling 138 can be a ring that is positioned within a groove (e.g., recess 610 shown in FIG. 6) on the mounting member 136. The mounting member 136 can be can be cylindrical shaped. The groove or recess 610 can be located in different positions on the mounting member 136. The inner surface of the rotational coupling 138 can contact or sit on the outer surface of the mounting member 136 (see FIG. 6). In this regard, the rotational coupling 138 is rigidly coupled to the mounting member 136, and can rotate along path 115 around the mounting member 136. Movement of the rotational coupling 128 can be in either direction along path 115. In various embodiments, the rotational coupling 138 and, thus, finger bracket 140 can continuously rotate around the mounting member. In other, embodiments the amount of rotation may be limited to, for example, 180°.

Figure 3A:
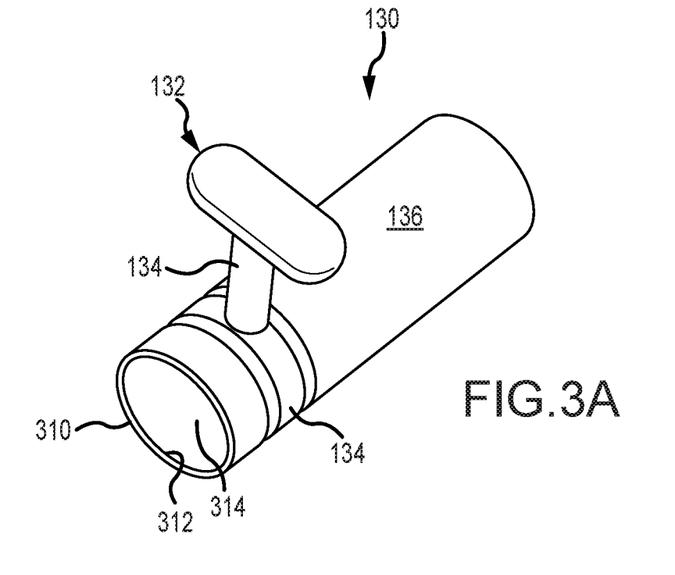
FIG. 3A illustrates, with a perspective view, a finger engagement assembly.

FIG. 3A illustrates an embodiment of just the finger engagement assembly 130 from a front perspective view. Specifically, the mounting member 136 is tubular shaped having an outer surface 310 and an inner surface 312. The inner surface 312 defines a cavity 314 extending through the mounting member 136. In various embodiments, the mounting member may be 0.5 inches long to 2 inches long. However, shorter or longer lengths are possible. The cavity 314 is sized such that the mounting member 136 can slide over and then be securely retained on a dental mirror 120. That is, in various embodiments, the cavity has a cross-sectional diameter that is 1 to 10% smaller than the diameter of the dental mirror handle 122.

In alternative embodiments, the mounting member can comprise multiple components. More specifically, the mounting member 136 can be an assembly of an inner component and outer component. In this embodiment, the inner component forms the inner surface 312 and the outer component forms the outer surface 310. The inner and outer components may be joined in a variety of ways such as adhesives, friction fit, welding, mechanical mating, and/or the like. In other embodiments, the inner component can have various features, such as ribs extending the length of the inner surface 312, to facilitate coupling of the mounting member 136 with the handle 122 of the dental mirror 120. For example, the inner surface 312 may have ribs extending longitudinally along the length of the mounting member 136 that protrude or are raised in relation to other portions of the inner surface 312. These, raised and lowered sections can facilitate mounting the finger engagement assembly 130, such as by reducing resistance to sliding the finger engagement assembly 130 over the handle 122. In these embodiments, the outer component could be a bearing/bearing assembly. Specifically, the inner component is able to elastically expand to fit over the handle 122 of a dental instrument, while the other component can be a rigid structure such as a bearing (e.g., sleeve bearing) that doesn't change in size.

Figure 3B:
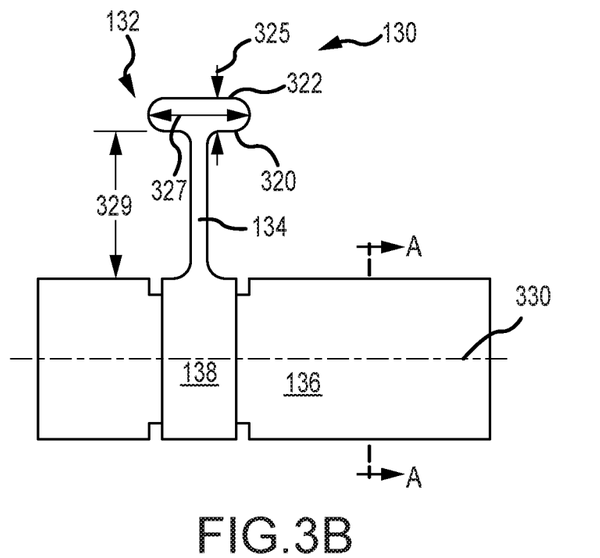
FIG. 3B illustrates, with a side view, a finger engagement assembly.

FIG. 3B illustrates a side view of the finger engagement assembly 130 and finger bracket 140. The crossbar 132 has a bottom surface 320, which would engage a user's fingers, and a top surface 322. The thickness 325 is defined as the distance between the bottom surface 320 and the top surface 322. The crossbar 132 also has a width 327 dimension. Typically, the thickness 325 of the crossbar can be from 0.03125 inches to 0.125 inches. Although other thicknesses are possible. The width 327 of the crossbar 132 is typically between 0.125 inches to 0.5 inches, with thicker or thinner widths possible. As shown, the bottom surface 320 is substantially flat and parallel to the grip axis 330. Typically, the post height 329 is between 0.375 inches and 0.75 inches. However, smaller or larger post heights 329 are possible. In various embodiments, the dimensions of the aforementioned features, depend on the materials that the finger bracket 140 is made from.

The finger bracket 140 and components thereof (e.g., post 134, crossbar 132, rotational coupling 138) can be formed from a variety of material, including without limitation, various polymers such as elastic rubbers, silicone rubbers, plastics, metals, and/or the like. For example, the post 134 can be made from a relatively more elastic material such as a rubber to allow the finger bracket to deform and adapt to differences in various user's hands. In such an embodiment, the post height 139 may be shorter compared to a more rigid material such as nylon because a rubber post will undergo more deformation at lower forces. In alternative embodiment, the thickness 325 can vary over the width 327 or length 142 (FIG. 1B). That is, portions of the crossbar 132 may be thicker or thinner depending on the location. For example, the bottom surface 320 may have semi-spherical recess running along its width 327 dimension to interface with the anterior side of a user's fingers 106, 108. In this embodiment, the spherical recesses can guide the user's finger into a desired position and help secure the user's hand to the dental instrument (e.g., dental mirror 120).

Figure 3C:
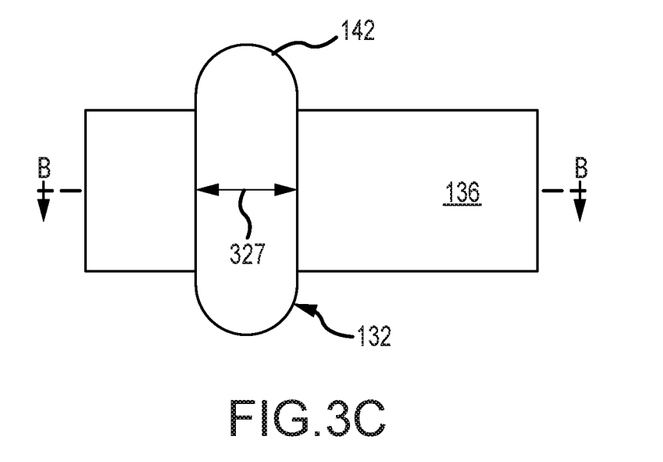
FIG. 3C illustrates, with a top view, a finger engagement assembly.

FIG. 3C illustrates a top view of the crossbar 132 when coupled to the mounting member 136. This view shows the width 327 and length 142 dimensions from a top perspective. Typically, the length 142 is between 0.5 inches to 1.5 inches. Although larger and smaller lengths 142 are contemplated. The width 327 can vary across the length 142 of the crossbar. For example, the width may be larger closer to the middle where the crossbar 132 connects to the post 134, and decrease towards the outer edges of the crossbar 132. In an alternative embodiment, the crossbar 132 can be semi-circular or arcuate shaped along its length and/or along its width.

Figure 4A:
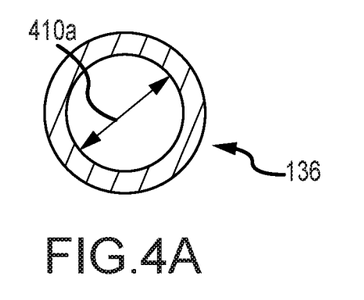
FIG. 4A illustrates, with an end cut-away view taken along ling A-A illustrated in FIG. 3B, the grip portion of a finger engagement assembly, when the finger engagement assembly is detached from a dental instrument.
Figure 4B:
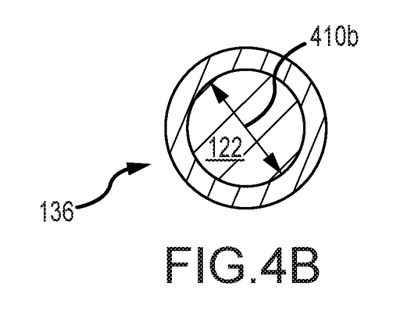
FIG. 4B illustrates, with an end cut-away view taken along line A-A illustrated in FIG. 3B, the grip portion of a finger engagement assembly, when the finger engagement assembly is mounted on the handle of a dental mirror.

FIG. 4A illustrates an end cut-away view taken along line A-A in FIG. 3B of the grip 130. Specifically, FIG. 4A illustrates the mounting member 136 in a first configuration before it is coupled with a dental instrument such as a dental mirror 120. In this embodiment, the mounting member 136 has a first inner diameter 410a. The first inner diameter 410a is sized to be slightly smaller (e.g., 1-10% smaller) than an outer diameter of the handle 122. The mounting member 136 is formed from an elastic material such that the first inner diameter 410a can expand. FIG. 4B shows the mounting member 136 when it is coupled with a handle 122. When placed over the handle 122, the inner surface of the mounting member 136 expands to a second inner diameter 410b. In this configuration the second inner diameter 410b is slightly larger than the first inner diameter 410a. In this regard, the elasticity in the mounting member 136 helps secure and retain the mounting member 136 in a fixed location on the handle 122. The first inner diameter 410a and material of the mounting member 136 is chosen such that a user can slide the mounting member 136 over the handle 122 and the mounting member is subsequently retained on the handle 122 in the position chosen by the user due to forces applied by the inner surfaces or wall of the mounting member 136 as it tries to elastically return to its at rest shape/ID. In alternative embodiment, other means of the retaining the mounting member 136 on the handle 122 are possible. For example, the mounting member 136 could have features such as a protrusion or key on its inner surface 312 that engages with a feature on the handle 122, such as a groove for receiving the protrusion or key. In other embodiment, adhesives, welding, fasteners, and/or the like can also be used to couple the mounting member 136 to the handle 122.

Figure 5A:
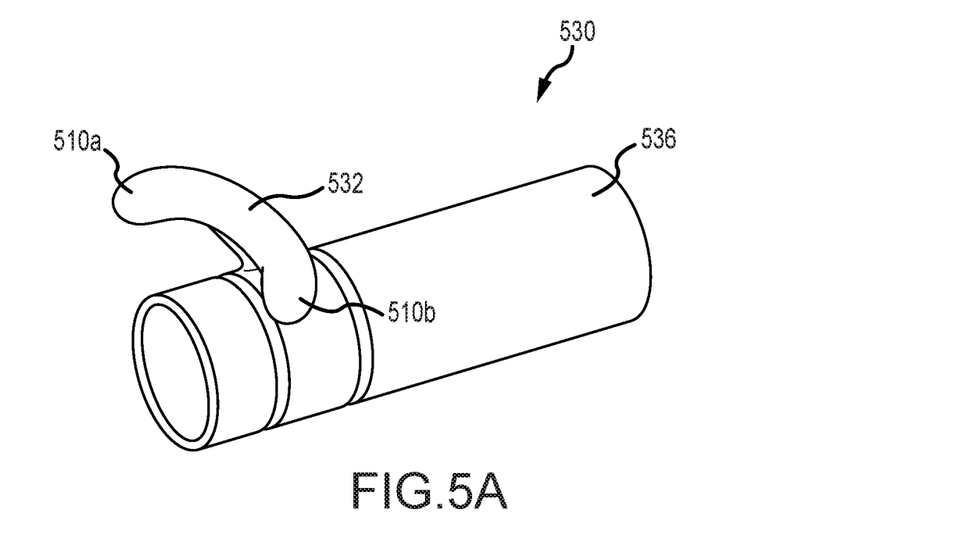
FIG. 5A illustrates, with a perspective view, another embodiment of a finger engagement assembly.
Figure 5B:
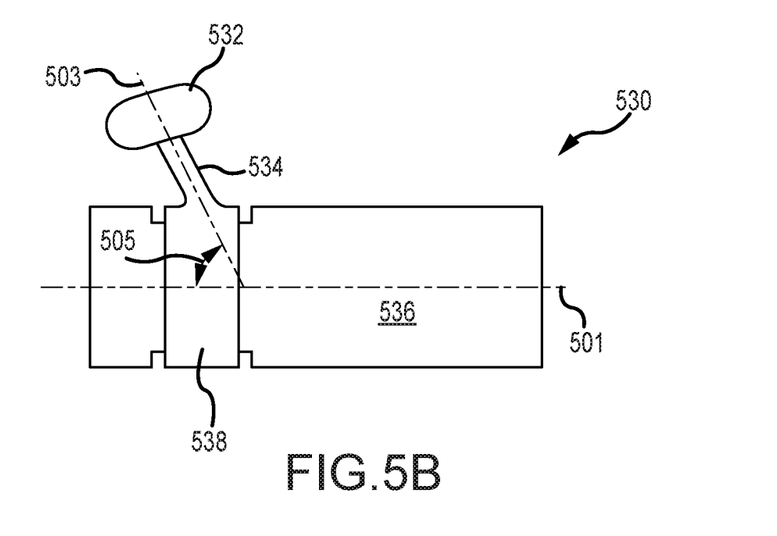
FIG. 5B illustrates, with a side view, the embodiment of the finger engagement assembly shown in Fig. A.

FIGS. 5A and 5B illustrate another embodiment of the finger engagement assembly 530. This embodiment illustrates a crossbar 532 having curved ends 510a and 510b (hereafter referred to 510 unless specifically referenced). Specifically, the ends 510 are curved downward toward the mounting member 536. In this regard, when a user is holding the grip 530 and the grip 530 is mounted on a dental mirror 120, the curved ends 510 wrap around the sides of the fingers 106, 108 to provide additional engagement of the crossbar 532 with the user's hand 102. Also illustrated in this embodiment, the post 534 and crossbar 532 are in an angled orientation relative to the mounting member 536. As shown in FIG. 5B, the mounting member 536 has a mounting member axis 501 extending the length of the mounting member 536 along its longitudinal axis. The post 534 has a post axis 503 extending the length of the post 534 along it longitudinal axis. In this embodiment, angle 505 is formed between the mounting member axis 501 and post axis 503. The angle is less than 90 degrees and typically ranges from 45 degrees to 85 degrees.

Figure 6:
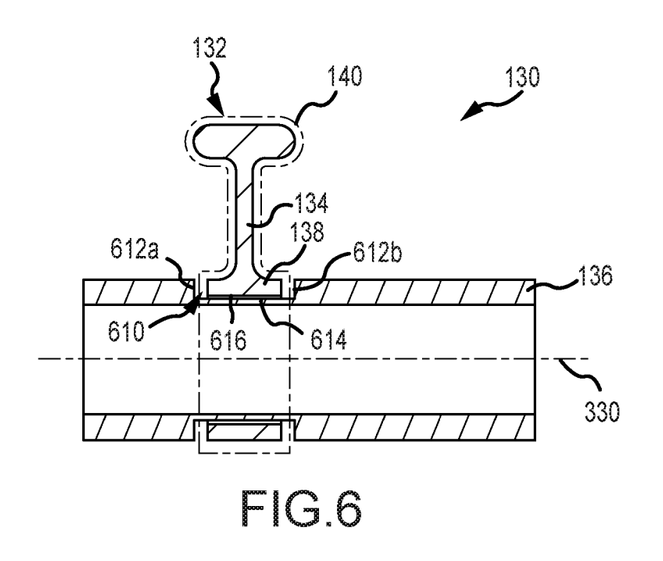
FIG. 6 illustrates, with a cut-away side view taken along line B-B illustrated in FIG. 3C, a finger engagement assembly.

FIG. 6 is a side cut-away view taken along line B-B shown in FIG. 3C, according to various embodiments. Specifically, mounting member 136 has a recess 610 located a first location along the mounting member 136. The recess is sized to receive the rotational coupling 138 of the finger bracket 140. The recess 610 has side walls 612a, 612b that retain the rotational coupling 138 in the recess 610 and mounting surface 614. The recess 610 and rotational coupling 138 are ring shaped and, thus, the finger bracket 140 is able to rotate relative to the mounting member 136. Specifically, the rotational coupling 138 has bottom surface 616 that contacts and/or surrounds mounting surface 614. The recess 610 is shaped to form a complimentary cavity to accept the rotational coupling 138.

Specifically, in this embodiment, as illustrated in the side cut-away view, the recess 610 is a rectangular groove in the outer surface 310 of mounting member 136 that extends about the grip axis 330. The recess 610 receives rotational coupling 138. The rotational coupling 138 can also have a rectangular profile, sized slightly smaller than the recess 610 that inserts or sits in the recess 610. When a user rotates the finger bracket 140 relative to the mounting member 136, bottom surface 616 slides over the mounting surface 614. Thus the frictional properties of these surfaces can be chosen to allow the finger bracket 140 to rotate using more or less force. For example, it may be desirable for the finger bracket 140 to freely rotate around the mounting member 136 with minimal force. In such an embodiment both the mounting surface 614 and bottom surface 616 can be materials that have low coefficients of friction such as polytetrafluoroethylene. In other embodiments, in can be desirable to require greater force to rotate the finger bracket 140 relative to the mounting member 136. This can be accomplished by having the mounting surface 614 and the bottom surface 616 be of higher friction materials to increase the resistance to rotation between these components. In yet other embodiments, the mounting surface 614 and/or the bottom surface 616 can have ridges, bumps, channels, or other features that function to inhibit rotation. Further, features such as these can provide registered positions of the finger bracket 140 relative to the mounting member 136.

In alternative embodiments, the recess 610 and rotational coupling 138 can have features to couple these components and facilitate rotation of the rotational coupling 138 relative to the mounting member 136. For example, one or more of the sidewalls 612 can be angled inward toward the center of the recess and the outer sides of the rotational coupling 138 can have an opposite angle/taper. The taper on sidewalls 612 overlaps the ends of the rotational coupling 138 to retain the rotational coupling 138 within the recess 610.

In other embodiments, the rotational coupling 138 can include additional components. For example the rotational coupling 138 could be a bearing, such as a ball-bearing, sleeve bearing, and/or the like. The bearing can rigidly couple with the mounting member 136, such as through a friction fit over the outer surface 310. Post 134 can then mount to the bearing to create a system where the post 134 rotates relative to the mounting member 136 and, thus, dental mirror 120. In another embodiment, the bearing can mount directly on the dental mirror handle 122.

I claim:

1. A finger engagement assembly for securing a handheld dental tool to a user's hand, comprising:
   a mounting member extending along a grip axis from a first end to a second end, wherein the mounting member has an outer surface and an inner surface; and
   a finger bracket comprising:
      a rotational coupling extending about the mounting member, wherein the rotational coupling is attached to the mounting member such that it can rotate about the grip axis;
      a post having a first end and a second end, wherein the first end is rigidly attached to the rotational coupling, the post extending from the rotational coupling in a first direction; and
      a crossbar attached to the second end of the post and spaced from the rotational coupling, the crossbar having a top surface and a bottom surface, wherein the bottom surface is elastically coupled to the post.

2. The finger engagement assembly of claim 1, wherein the mounting member is an elongated cylinder, the inner surface defines an aperture adapted for mating with and retaining a handheld dental instrument, and the outer surface has an annular recess for receiving the rotational coupling.

3. The finger engagement assembly of claim 2, wherein the rotational coupling is a ring sized to fit within the annular recess, such that the finger bracket is rigidly coupled with the mounting member.

4. The finger engagement assembly of claim 2, wherein the first direction is substantially normal to the grip axis.

5. The finger engagement assembly of claim 2, wherein the first direction is a vector oriented between 45 degrees to 90 degrees in relation to the grip axis.

6. The finger engagement assembly of claim 2, wherein, when the finger engagement assembly is coupled with a dental mirror and held by a user, the dental mirror is positioned at least partially between a first contact point on a user's first finger, a second contact point on a user's second finger and a third contact point on a user's thumb and the back surface of the crossbar contacts a fourth contact point on the first finger and a fifth contact point on the second finger.

7. The finger engagement assembly of claim 5, wherein the first contact point and fourth contact point are located on opposite sides of the first finger, and the second contact point and fifth contact point are located on opposite sides of the second finger.

8. The finger engagement assembly of claim 1, wherein the post is operable to be elastically deformed.

9. An apparatus for supporting a dental mirror in a user's hand, comprising:
   a mounting member including a tubular body for receiving a handle of the dental mirror;
   a finger bracket for mating with fingers of the user's hand; and
   a rotational coupling assembly attached to an outer surface of the mounting member, wherein the finger bracket extends outward from the rotational coupling and wherein, during use, the rotational coupling assembly operates to allow the finger bracket to rotate at least 180 degrees about a central axis of the tubular body of the mounting member.

10. The apparatus of claim 9, wherein the tubular body is formed of an elastomer.

11. The apparatus of claim 9, wherein the rotational coupling assembly comprises an inner element attached to the mounting member and an outer element rotatably coupled to the inner element and wherein the finger bracket is rigidly coupled to the outer element of the rotational coupling assembly.

12. The apparatus of claim 11, wherein the outer element of the rotational coupling assembly is rotatable in either direction for 360 degrees relative to the inner element of the rotational coupling assembly.

13. The apparatus of claim 9, wherein the finger bracket comprises a post extending from a first end attached to the rotational coupling assembly to a second end spaced apart a distance from the rotational coupling assembly and wherein the finger bracket further comprises an elongated cross bar attached to the second end of the post to be transverse to a longitudinal axis of the post.

14. The apparatus of claim 13, wherein the post has a length of at least 0.5 inches and extends outward at an angle in the range of 45 to 90 degrees as measured between the longitudinal axis of the post and a central axis of the tubular body.

15. The apparatus of claim 13, wherein at least one of the post and the cross bar is flexible and formed of a plastic or elastomeric material.

16. The apparatus of claim 13, wherein the cross bar has a length of at least 0.75 inches, is attached at a center point to the second end of the post.

17. A finger engagement assembly for securing a handheld dental tool to a user's hand, comprising:
   a mounting member with an outer surface and an inner surface; and
   a finger bracket comprising:
      a rotational coupling extending about the mounting member, wherein the rotational coupling is rotatably attached to the mounting member;
      a post having a first end and a second end, wherein the first end is rigidly attached to the rotational coupling, the post extending from the rotational coupling in a first direction; and
      a crossbar attached to the second end of the post and spaced from the rotational coupling, the crossbar having a top surface and a bottom surface, wherein the bottom surface is elastically coupled to the post,
      wherein the mounting member is an elongated cylinder, the inner surface defines an aperture adapted for mating with and retaining a handheld dental instrument, and the outer surface has an annular recess for receiving the rotational coupling, and wherein the rotational coupling is a ring sized to fit within the annular recess, such that the finger bracket is rigidly coupled with the mounting member.

18. The finger engagement assembly of claim 17, wherein the first direction is a vector oriented between 45 degrees to 90 degrees in relation to a longitudinal axis of the mounting member.

19. The finger engagement assembly of claim 17, wherein the post is elastically deformable.

20. The apparatus of claim 17, wherein at least one of the post and the cross bar is flexible and formed of a plastic or an elastomeric material.

* * * * *